(12) United States Patent
Cain et al.

(10) Patent No.: US 11,896,769 B2
(45) Date of Patent: *Feb. 13, 2024

(54) UNIVERSAL RESPIRATORY DETECTOR

(71) Applicant: Affirm Medical Technologies II, LLC, Piedmont, CA (US)

(72) Inventors: Janice Cain, Piedmont, CA (US); Brian Scott Cain, Piedmont, CA (US); Alicia B. Dreger, Pleasant Hill, CA (US); Mark J. Bernhard, Alamo, CA (US); Avinash A. Mohan, Yorktown Heights, NY (US)

(73) Assignee: Affirm Medical Technologies II, LLC, Piedmont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/145,682

(22) Filed: Dec. 22, 2022

(65) Prior Publication Data

US 2023/0130869 A1 Apr. 27, 2023

Related U.S. Application Data

(63) Continuation of application No. 17/350,737, filed on Jun. 17, 2021, now Pat. No. 11,554,237.

(60) Provisional application No. 63/040,372, filed on Jun. 17, 2020.

(51) Int. Cl.
*A61M 16/10* (2006.01)
*G01N 21/78* (2006.01)

(52) U.S. Cl.
CPC ....... *A61M 16/1005* (2014.02); *G01N 21/783* (2013.01); *A61M 2016/103* (2013.01); *A61M 2205/584* (2013.01)

(58) Field of Classification Search
CPC ........ A61M 16/1005; A61M 2016/103; A61M 2205/584; G01N 21/783
See application file for complete search history.

(56) References Cited

U.S. PATENT DOCUMENTS

| | | | |
|---|---|---|---|
| 3,420,635 | A | 1/1969 | Davis |
| 4,256,694 | A | 3/1981 | McAllister et al. |
| 4,728,499 | A | 3/1988 | Fehder |
| 4,879,999 | A | 11/1989 | Leiman et al. |
| 5,005,572 | A | 4/1991 | Reamer et al. |
| 5,156,159 | A | 10/1992 | Lampotang et al. |
| 5,179,002 | A | 1/1993 | Fehder |
| 5,857,460 | A | 1/1999 | Popitz |
| 6,196,223 | B1 | 3/2001 | Belfer et al. |
| 6,436,347 | B1 | 8/2002 | Cedeon |

(Continued)

FOREIGN PATENT DOCUMENTS

| | | |
|---|---|---|
| WO | WO2012/064540 A2 | 5/2012 |
| WO | WO2020/019915 A1 | 6/2020 |

*Primary Examiner* — Colin W Stuart
*Assistant Examiner* — Matthew D Ziegler
(74) *Attorney, Agent, or Firm* — Shay Glenn LLP

(57) ABSTRACT

A universal respiratory detector for detecting a respiratory gas. The universal respiratory detector may include a plurality of layers with a visual indicator to quickly and reversibly change color to detect a respiratory gas parameter such as carbon dioxide. The color change may be visible from both sides of the detector. In some examples, the respiratory detector may be a biocompatible and conformable sticker for mounting on a person's face or an oxygen delivery device.

20 Claims, 10 Drawing Sheets

(56) References Cited

U.S. PATENT DOCUMENTS

| | | |
|---|---|---|
| 6,502,573 B1 | 1/2003 | Ratner |
| 6,584,974 B1 | 7/2003 | Ratner |
| 6,651,661 B2 | 11/2003 | Matioc |
| 7,246,622 B2 | 7/2007 | Geist |
| 7,811,276 B2 | 10/2010 | O'Neil et al. |
| 8,062,221 B2 | 11/2011 | Debreczeny et al. |
| 8,396,524 B2 | 3/2013 | Ostrowski |
| 9,044,562 B2 | 6/2015 | Dillingham et al. |
| 10,175,254 B2 | 1/2019 | Mace et al. |
| 10,849,375 B1 * | 12/2020 | Bowen ............... A41D 13/1115 |
| 10,856,790 B2 | 12/2020 | Shekarriz et al. |
| 11,554,237 B2 | 1/2023 | Cain et al. |
| 2003/0127102 A1 | 7/2003 | Strawder et al. |
| 2003/0199095 A1 | 10/2003 | Yuyama et al. |
| 2004/0223876 A1 | 11/2004 | Kirollos et al. |
| 2006/0216828 A1 | 9/2006 | Ratner et al. |
| 2009/0250061 A1 | 10/2009 | Marasigan |
| 2011/0094514 A1 | 4/2011 | Rakow et al. |
| 2012/0048278 A1 | 3/2012 | Yasick |
| 2012/0136267 A1 | 5/2012 | Derrick et al. |
| 2017/0281991 A1 | 10/2017 | Wang et al. |
| 2018/0110951 A2 | 4/2018 | Beard |
| 2020/0038617 A1 | 2/2020 | Varga et al. |

\* cited by examiner

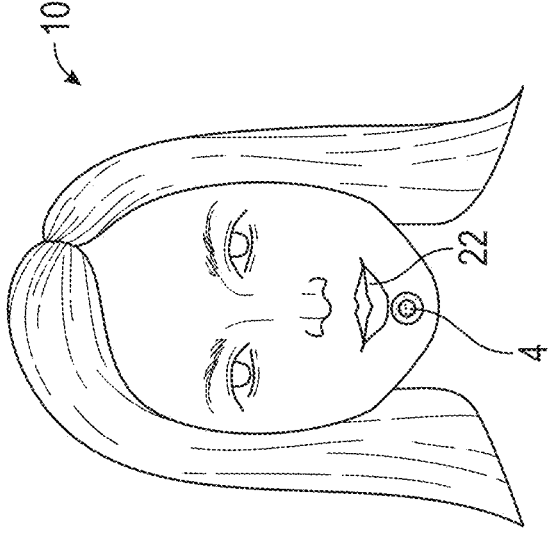
FIG. 1A
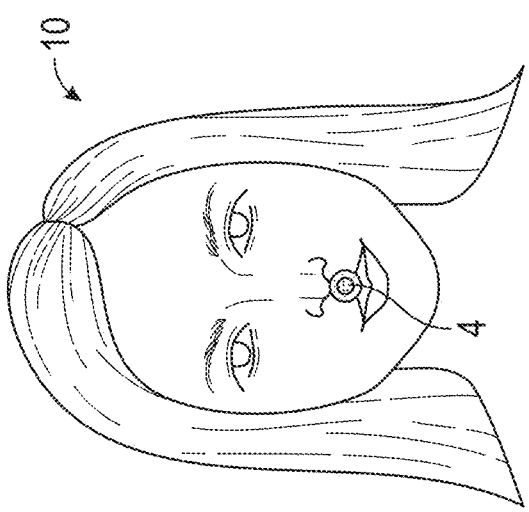
FIG. 1C
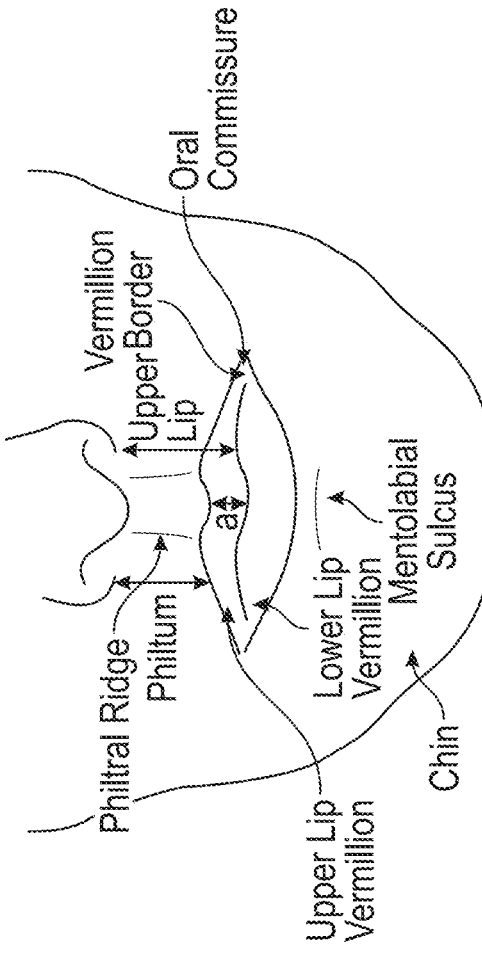
FIG. 1B
FIG. 1D

UNIVERSAL RESPIRATORY DETECTOR

CROSS REFERENCE TO RELATED APPLICATIONS

This application is a continuation of U.S. application Ser. No. 17/350,737, filed Jun. 17, 2021, which claims the benefit of U.S. Provisional Application No. 63/040,372, filed Jun. 17, 2020, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are sensors useful for detecting breathing. In particular, described herein are sensors for detecting a respiratory parameter such as a respiratory gas from an individual, and displaying a visual signal indicative of the breathing status of the individual based on the detected respiratory parameter.

BACKGROUND

Oxygen is essential to life. Human beings cannot store very much oxygen in their bodies. Regular breathing, referred to as ventilation, for supplying oxygen to the body is important to sustain body functions. Permanent brain damage can occur after a person stops breathing for as little as three minutes and death can occur a few more minutes after that unless ventilation is restored. Insufficient breathing, such as shallow or irregular breathing, can lead to insufficient oxygen and problems such as headaches, confusion, shortness of breath, weakness, and poor heart and brain function.

The chest rises up and down during breathing and one way of monitoring breathing is to observe adequate chest rise. However, chest rise can be subtle and difficult to observe, such as if person is covered by a blanket, wearing bulky clothes, in a poorly lit area, or has shallow breathing. Some hospitals monitor a patient's breathing status using a specially designed monitoring device for monitoring air exhaled from the patient. Commonly used monitoring devices measure and numerically or graphically display the amount or concentration of carbon dioxide in exhaled air. These devices variably have air sampling lines, detectors, displays, batteries or another power source and may need to be mounted on a device that supplies oxygen to the patient. For example, monitoring devices are commonly used by anesthesiologists by attaching a monitoring device to a tube placed in the patient's airway (an intubated patient) and taking a sample of the exhaled air during surgery or by medical personnel taking a sample of expired air from an oxygen face mask. These monitoring devices are limited in the circumstances in which they can be used and require training for proper use. These devices are subject to contamination by viruses and other biologic agents. They can also be bulky, relatively expensive, difficult to decontaminate, or require warm up time. Another monitoring device is a patch mounted on a device that supplies oxygen to the patient. These patches can be bulky, have a short life span, and require an oxygen-supplying device for attachment.

Accordingly, there is a need for improved devices for monitoring breathing to overcome these and other problems. Described herein are systems, devices and methods for determining a person's breathing status that may address these and other problems.

SUMMARY OF THE DISCLOSURE

One aspect of the disclosure provides universal respiratory detector for detecting a respiratory gas and displaying a respiratory status based on the gas, the respiratory detector including a first side and a second side; a cover layer; and a respiratory sensor layer comprising a backing and a visual indicator on the backing, the visual indicator configured to reversibly change color when a respiratory gas parameter changes and to display the color change wherein the color change is visible from both the first side and the second side and wherein the cover layer covers at least part of the backing. Some detectors include an adhesive ring on the second side, the adhesive ring adhering the respiratory sensor layer to the cover layer, the adhesive ring comprising a center region configured to allow a respiratory air to flow therethrough, In some embodiments, the universal respiratory detector is a sticker. In some embodiments, the universal respiratory detector is configured to conform to a curved or variable surface contour of an oxygen delivery device or a face of a user and flex and move together with movement of the oxygen delivery device or a face of a user.

In some embodiments, the universal respiratory detector includes a low or no off-gassing adhesive on the adhesive ring. Some embodiments of universal respiratory detector further include a biocompatible adhesive on the cover and a release liner on top of the biocompatible adhesive.

In some embodiments, the universal respiratory detector the backing includes polyethersulfone, polysulfone, or polyphenylene sulfone.

In some embodiments, the universal respiratory detector has a maximum thickness less than 0.1 inches. In some embodiments, the universal respiratory detector has a longest dimension of less than about 1 inch.

In some embodiments, the universal respiratory detector is configured to reversibly change color in response to carbon dioxide.

In some embodiments, the universal respiratory detector is biocompatible.

In some embodiments of the universal respiratory detector, the adhesive ring includes a transparent or translucent membrane in the middle.

In some embodiments of the universal respiratory detector, the visual indicator is configured to reversibly change color when a respiratory gas parameter changes and to display the color change for a period of time lasting at least 10 minutes, at least one hour, at least ten hours, at least one day, at least three days, at least one week, or at least two weeks.

In some embodiments of the universal respiratory detector, the detector is non-metallic, latex free and configured to be single use and disposable.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A-FIG. 1C shows examples of universal respiratory detectors applied to different parts of an individual's face for detecting a respiratory gas from the individual.

FIG. 1D shows the anatomy of a face.

FIG. 6A shows a top view of the universal respiratory detector. For clarity, the transparent cover 86 on the top is omitted from this view. FIG. 6B shows a top view of the universal respiratory detector including the clear film 86 on top. The middle circles show areas of overlap of layers. FIG. 6C shows an exploded view of the detector and how the differing diameters work together to create a versatile and easy to manufacture detector.

DETAILED DESCRIPTION

Figure 2A:
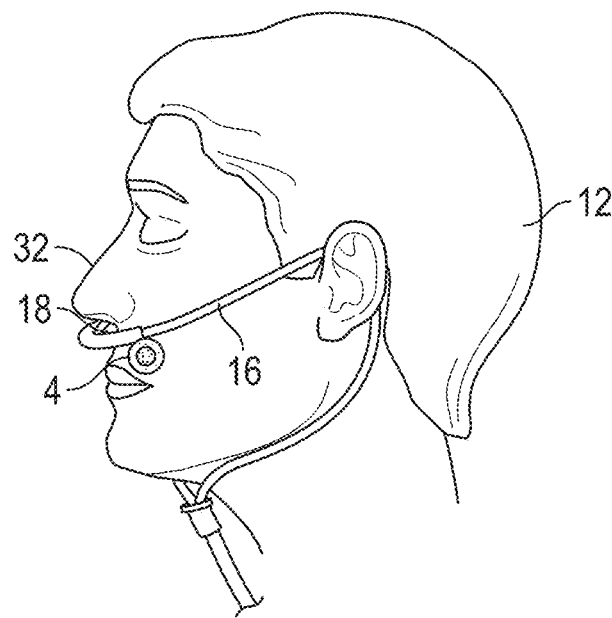
FIG. 2A shows a universal respiratory detector for detecting a respiratory gas on the face of an individual using an oxygen cannula for receiving a supply of oxygen.

Described herein are systems, devices, and methods useful for determining if an individual is breathing and if breathing is adequate. The systems, devices, and methods described herein may be useful for detecting a respiratory characteristic, such as a carbon dioxide gas level in respired gas, and for displaying a respiratory status of an individual based on detecting the respiratory characteristic to indicate if the individual is adequately breathing. The devices described herein provide rapid response visual detectors that respond to changes in breathing and rapidly display signals in response to the changes (such as with transition times of less than ½ second). The devices described herein may replace existing devices for detecting breathing status, as well as provide novel solutions for currently unmet needs. The devices herein may sometimes be referred to as universal respiratory detectors as these detectors may be useful for detecting a respiratory characteristic (such as carbon dioxide or another respiratory gas) under a broad range of health conditions, environmental conditions, and situations. A universal respiratory detector as described herein may be adapted to conform to and adhere to a range of different types of surface and surface compositions, including various dry surfaces such as facial skin and oxygen delivery devices. A visual indicator of a universal respiratory detector may be double-sided and can be viewed from either side. The universal respiratory detector configured for easy application to a surface, sometimes by removing a release and sticking the universal respiratory detector to a surface. A universal respiratory detector as described herein may be useful for individuals regardless of personal characteristics (young, old, with facial hair, without facial hair, intubated, non-intubated, in a hospital, in a public place, etc.) and regardless of whether the individual uses a respiratory aid (e.g., a face mask, an oxygen delivery cannula, a CPAP mask, a trache collar, a hyperbaric chamber) or does not use a respiratory aid. A universal respiratory detector as described herein can be very low-profile, comfortable, and easy to wear and use. Thus a home medicine cabinet, first aid kit, car, combat hospital, ambulance, or clinic may need to stock only one or very few types of respiratory detector. Additionally, a universal respiratory detector as described herein may be easy for anyone to apply. A family member, friend, or healthcare worker can apply the respiratory detector to individuals. An individual can apply it on themselves.

FIG. 1A shows a universal respiratory detector with a circular universal respiratory detector 4 placed below the nose or nostril of an individual 10 and above the upper lip region on the philtum, for detecting a respiratory characteristic, such as carbon dioxide in exhaled breath. Carbon dioxide, a respiratory gas, may be used in this disclosure by way of example of a respiratory parameter for ease of explaining, although any of the universal respiratory detectors described herein may alternatively or additionally detect other respiratory characteristics or gases (e.g., pH of exhaled gas, oxygen concentration). Below the nostril may be a good place to detect a respiratory gas expelled from the nostril.

Figure 2B:
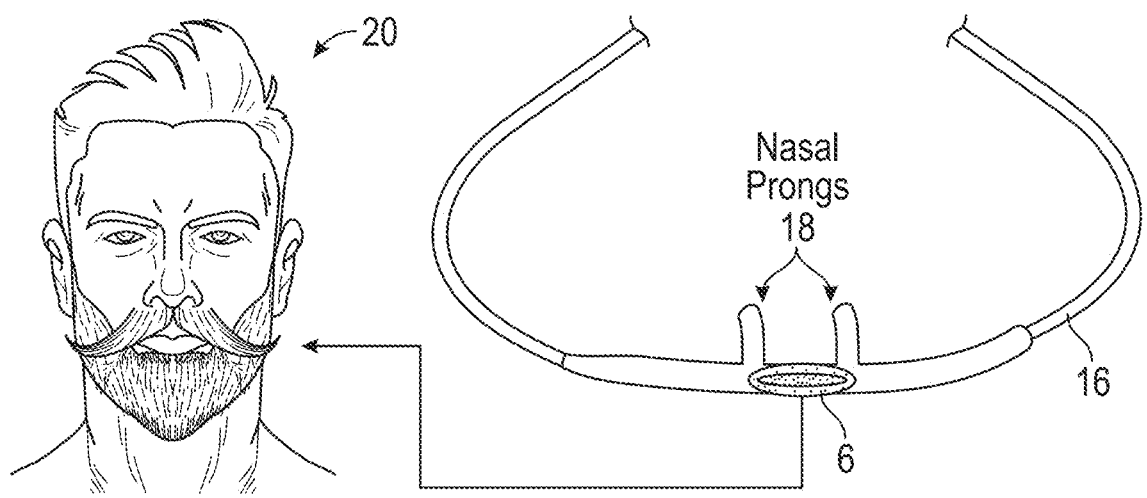
FIG. 2B shows a nasal cannula similar to the one shown in FIG. 2A ready for use for a man with facial hair. The universal respiratory detector for detecting a respiratory gas is adhered to an outside surface of the nasal cannula.
Figure 2C:
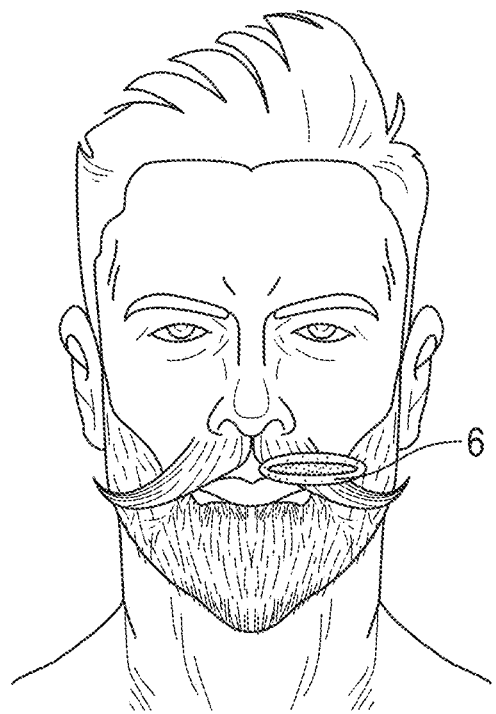
FIG. 2C shows a man with facial hair with a universal respiratory detector attached to his moustache.
Figure 9:
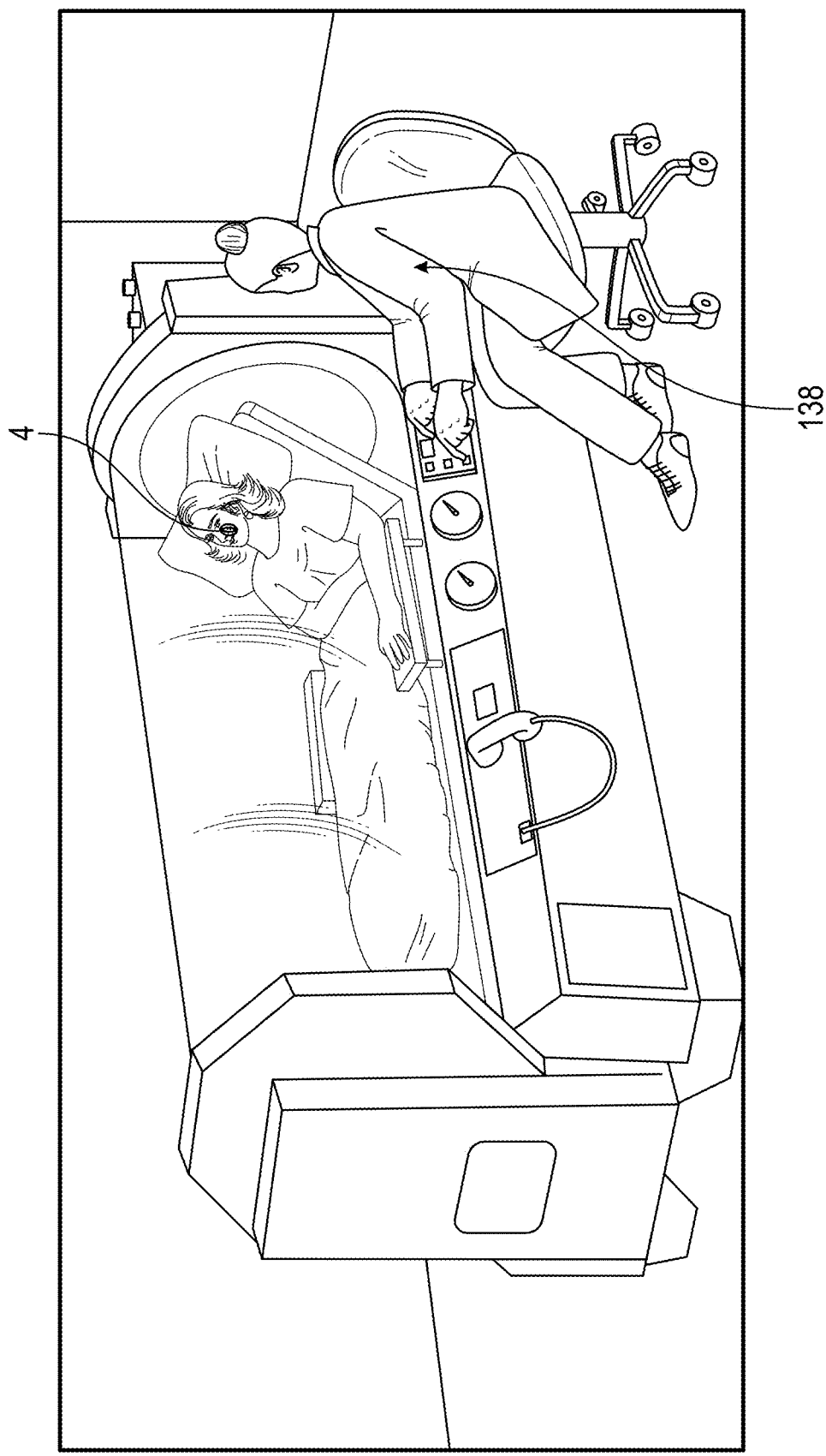
FIG. 9 shows an individual in a containment chamber with a universal respiratory detector applied to the nasal area, and a health care professional viewing the detector to determine the breathing status of the individual.

As explained in more detail below, the universal respiratory detector 4 has a respiratory indicator configured to reversibly respond such as to change color when a respiratory gas parameter changes and to display a visual signal such as color change based on the response. The respiratory indicator may be configured to reversibly respond quickly, such as with each breath. The respiratory indicator may be configured to reversibly respond within ½ second. A universal respiratory detector may be configured to conform to and attach to various surfaces. A universal respiratory detector may be biocompatible and include a biocompatible adhesive so it can be attached to a person's face and skin, and stay in place for hours or days without little or no irritation. A universal respiratory detector may be removable so it can be removed from a person's face and skin with little or no damage to the face and skin. As seen in FIG. 1D, the face, and in particular the region around the nose and mouth has complex geometry, with various dips and extensions and abruptly changing concave and convex surfaces. FIG. 1D shows the philtrum under the nose extending and dipping at the philtral ridge. FIG. 1A shows universal respiratory detector 4 resting against the contours of the irregular skin surface, conforming to the convex and concave surfaces. When a person breathes through their nose, the air exits from a nostril in the nose, and the region under the nostril and near the nostril may be a good location for a respiratory detector. However, some individuals may breathe out through their mouth or may not be able to wear a respiratory detector directly below or near their nose such as due to an injury. FIG. 1B shows a respiratory detector for detecting a respiratory gas with circular universal respiratory detector 4 on the chin 24 of the individual 10. FIG. 1D shows chin anatomy in more detail. A chin has round or egg shape, with a crease in the chin, referred to as the mentolabial sulcus. The universal respiratory detector 4 is configured to conform to the round or egg shape as well as the crease to provide a smooth and comfortable fit. FIG. 1C shows another variation of a respiratory detector for detecting a respiratory gas with an ovoid shaped universal respiratory detector 6 below both nostrils and crossing the philtrum and philtral ridge of the individual 10. In other variations, more than one universal respiratory detector may be applied to an individual, such as one below each nostril, or one below the nose and one below the lips, which may be useful for detecting a respiratory gas from an individual who sometimes breathes out of his or her nose and sometimes out the mouth. FIGS. 1A-1C show individuals in need of respiratory air monitoring who are not using a supplemental oxygen source. The respiratory detectors described herein may be especially useful for assessing and/or monitoring breathing status for an individual having or suspected of having an infectious disease (e.g., Avian flu, covid-19, chickenpox, Ebola, influenza, Middle Eastern Respiratory Syndrome (MERS), Severe Acute Respiratory Syndrome (SARS)). The respiratory detectors described herein can be applied and assessed/monitored with minimal contact between a caregiver and a potentially infectious individual, and in particular, their breath. FIG. 9 shows an individual in a containment chamber with a respiratory sensor 4 visible by a medical personnel 138. The respiratory detectors described herein can be used without a need for sterilizing or discarding expensive equipment. The respiratory detectors described herein could be useful for rapidly assessing and/or monitoring an individual who is suspected of having an illness or recovering from an illness, sleep apnea or other disordered sleep breathing condition, a seizing (e.g., epileptic) individual, experiencing bronchospasm (e.g., asthma, COPD, an allergic reaction). The respiratory detectors described herein may help recognize airway obstructions before the individual shows signs of attack. The respiratory detectors described herein may be useful for triaging and rapidly determining who needs supplemental oxygen or other aid, such as while triaging a group of individuals involved in an accident or an attack with multiple potential victims. These and other respiratory detectors described herein could be useful for assessing and/or monitoring insufficient breathing as well as excess breathing. The respiratory detectors described herein may be useful for assessing and/or monitoring treatment for an individual in respiratory distress or transporting individuals in an ambulance or other medical transport vehicle. The respiratory detectors described herein may be portable and small and not require any electrical source or battery power. Although FIGS. 1A-1C show an individual who is not using a supplemental oxygen source for breathing and the universal respiratory detector placed on the individual's face, a universal respiratory detector may be also used on an individual using a supplemental oxygen source and a detector may be placed on the supplemental oxygen source itself. FIG. 2A shows an individual 12 using an oxygen cannula 16 for oxygen delivery to the patient through prongs 18 placed in the nostrils in the individual's nose. FIG. 2A shows the individual 12 with universal respiratory detector 4 placed under the individual's nose 32. As shown, the universal respiratory detector 4 is offset from the midline of the individual, which may allow the universal respiratory detector 4 to be more easily visible to a health care professional (the detector is not obscured from view by the oxygen cannula 16). An offset position may prevent excess friction from the oxygen cannula 16 removing or irritating the universal respiratory detector 4. FIG. 2B shows an oxygen cannula 16 being readied for placement to individual 20 with facial hair. Facial hair may make placing a respiratory sensor 4 on appropriate skin surface of the individual 20 more difficult. Instead, the universal respiratory detector may be adhered to and wrapped partially, mostly, or all the way around part of the oxygen cannula 16. FIG. 2B shows the universal respiratory detector 4 adhered to a surface of the oxygen cannula 16. The universal respiratory detector 4 is readily visible to a health care provider or another individual who can readily ascertain if the universal respiratory detector is visually changing, e.g., changing color, indicative of whether or not the person is breathing. FIG. 2C shows the universal respiratory detector 4 attached to the facial hair (moustache) of the individual 20. A sticker-type detector as described herein may be well-suited for this and other indications.

Figure 3A:
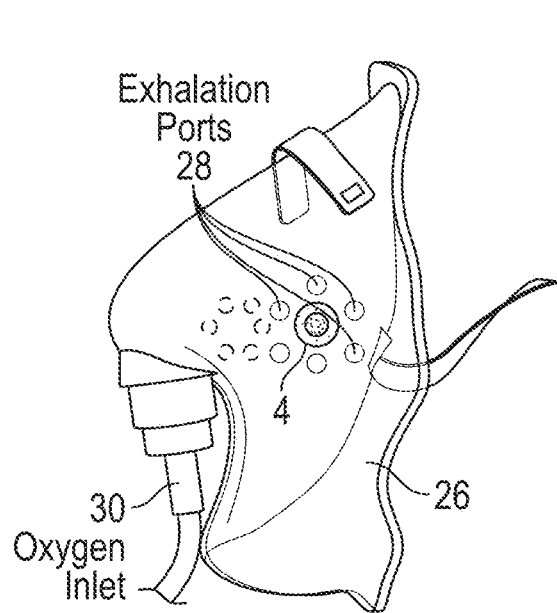
FIG. 3A shows a universal respiratory detector for detecting a respiratory gas adhered to the inside surface of an oxygen facemask. The rapidly reversible visual signal of the universal respiratory detector that responds to the presence or absence of the respiratory gas is readily visible to a health care provider or other individual looking at the facemask.
Figure 3B:
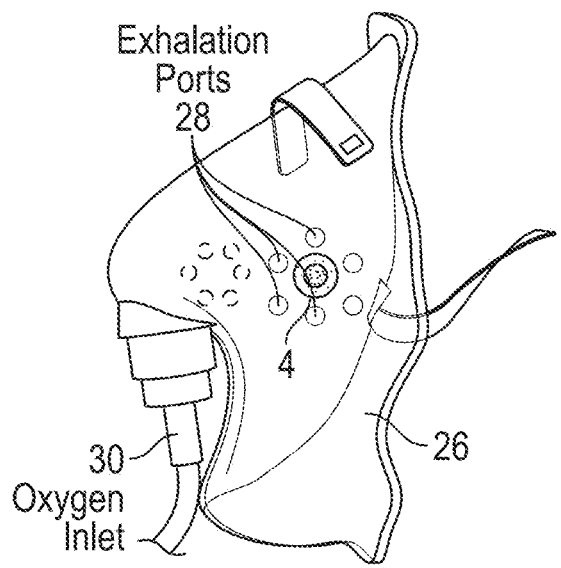
FIG. 3B shows a universal respiratory detector for detecting a respiratory gas adhered to the outside surface of an oxygen facemask similar to the one shown in FIG. 3A but the detector is mounted on the mask in opposite orientation relative to the detector shown in FIG. 3A. The rapidly reversible visual signal of the universal respiratory detector that responds to the presence or absence of the respiratory gas is readily visible to a health care provider or other individual looking at the facemask.
Figure 4A:
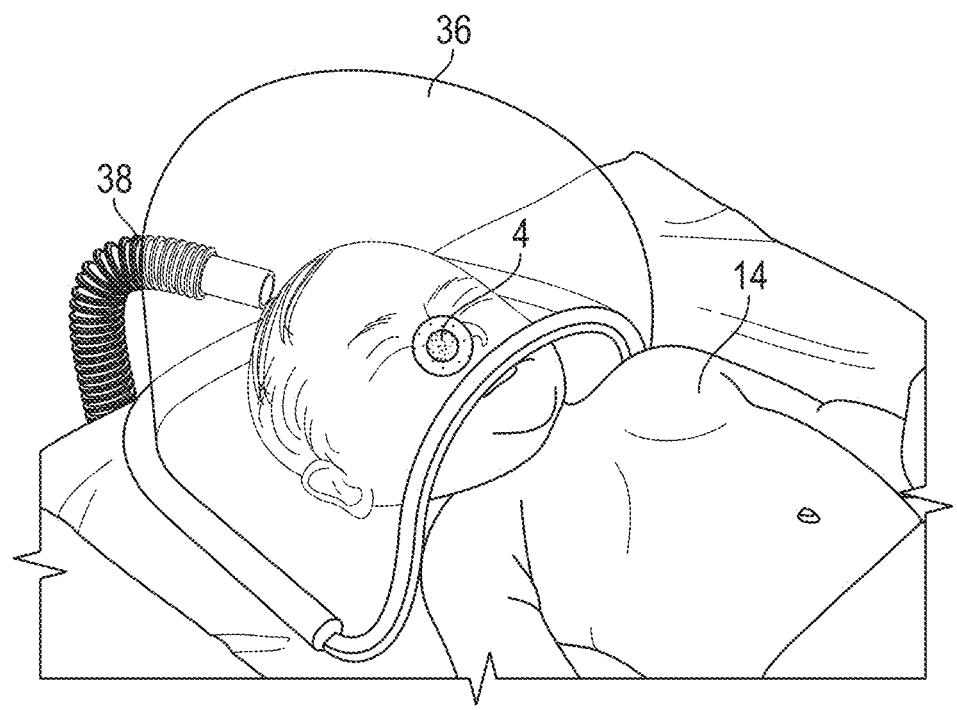
FIG. 4A shows a universal respiratory detector for detecting a respiratory gas adhered to the inside surface of an oxygen tent for an infant. The rapidly reversible visual signal of the universal respiratory detector that responds to the presence or absence of the respiratory gas is visible to a health care provider or individual looking at the tent.
Figure 4B:
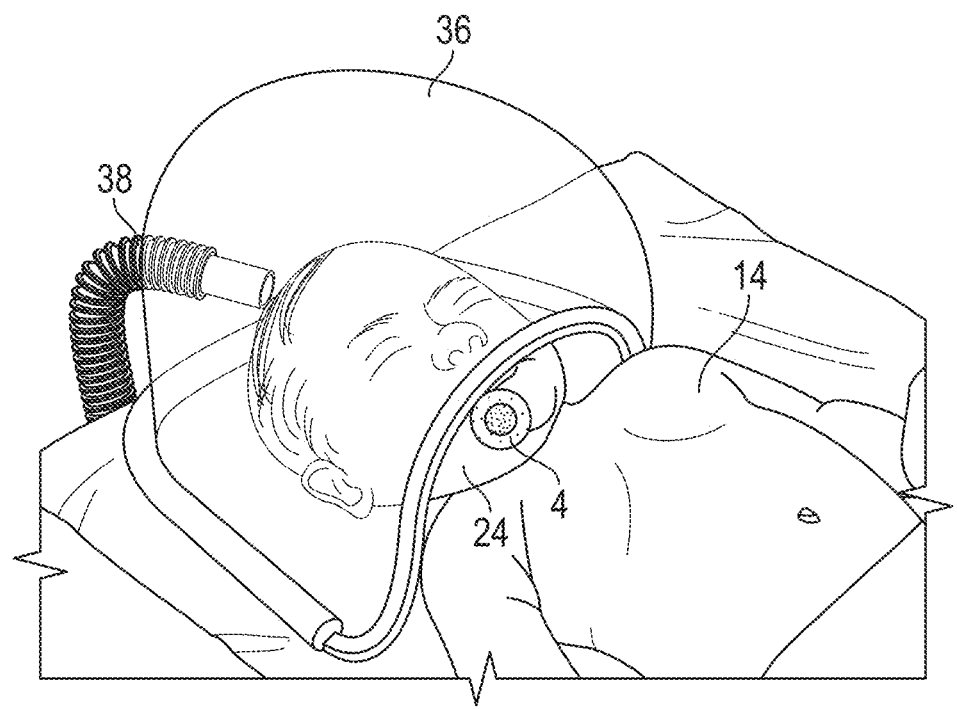
FIG. 4B shows a universal respiratory detector for detecting a respiratory gas adhered to the face of an infant. The infant is in an oxygen tent similar to the one shown in FIG. 4A, but the respiratory detector in FIG. 4B is adhered in the opposite orientation relative to the detector shown in FIG. 4A. The rapidly reversible visual signal of the universal respiratory detector that responds to the presence or absence of the respiratory gas is readily visible to a health care provider looking at the infant's face.

FIG. 3A shows an oxygen face mask 26 for placing over an individual's mouth and nose to provide oxygen to the individual. Oxygen enters the interior of the mask through oxygen inlet 30, which uses positive pressure to move the oxygen into the interior of the mask, where the oxygen can be inhaled by the individual. When the individual exhales, the expiratory gases exit from the individual into the mask and then exit out of the mask through exhalation ports 28. Since gases exit the mask through the exhalation ports 28, the area near the exhalation ports may be a good place for sampling and sensing expiratory cases from the individual. FIG. 3A shows circular universal respiratory detector 4 adhered to the inside of the oxygen face mask 26 for sensing expiratory gases from the individual. The oxygen face mask 26 is clear or translucent and the universal respiratory detector 4 is visible through the material of the mask. In particular, any color changes in the universal respiratory detector 4 are visible from outside the mask. This orientation may be considered a first orientation, relative to an observer, such as a health care provider, outside the mask. FIG. 3B shows the oxygen face mask 26 shown in FIG. 3A, except in this face mask the circular universal respiratory detector 4 is adhered to the outside of the mask rather than on inside. Of note, the circular universal respiratory detector 4 shown in FIG. 3B is in a second or opposite orientation and the universal respiratory detector 4 is "flipped over" relative to the circular universal respiratory detector 4 shown in FIG. 3A. As will be discussed in more detail below, the visual signal associated with the respiratory detector is visible from both sides. Thus, whether the universal respiratory detector is in the first orientation shown in FIG. 3A or in the second, "flipped over" orientation shown in FIG. 3B, the visual signal associated with the respiratory indicator is visible to an observer. Having a universal respiratory detector configured for mounting and visualization in either orientation simplifies use of the respiratory indicator, as the visual sensor can be detected regardless of how the detector is mounted. FIGS. 4A and 4B show another example of how circular universal respiratory detector 4 can be used in a first orientation or in a second "flipped over" orientation. FIGS. 4A and 4B show a baby 14 inside an oxygen tent 36. The oxygen tent 36 is provided with oxygen through oxygen inlet 38. FIG. 4A shows the universal respiratory detector 4 adhered or mounted to an inside surface of oxygen tent 36 in a first orientation, similar to the orientation shown in FIG. 3A. Similar to as described above in FIGS. 1A-1C, FIG. 4B shows the universal respiratory detector 4 adhered to a surface of the baby's face; in particular on chin 24 and in the opposite, or second orientation, compared with the universal respiratory detector 4 shown in FIG. 4A. A detector on an oxygen tent that is close to a face may readily receive exhaled air as the body expels respired air under pressure. Since the visual detector can be detected from both sides, an observer (medical personal or another individual) can readily assess breathing status regardless of detector orientation and can change from one detector to another.

Figure 5A:
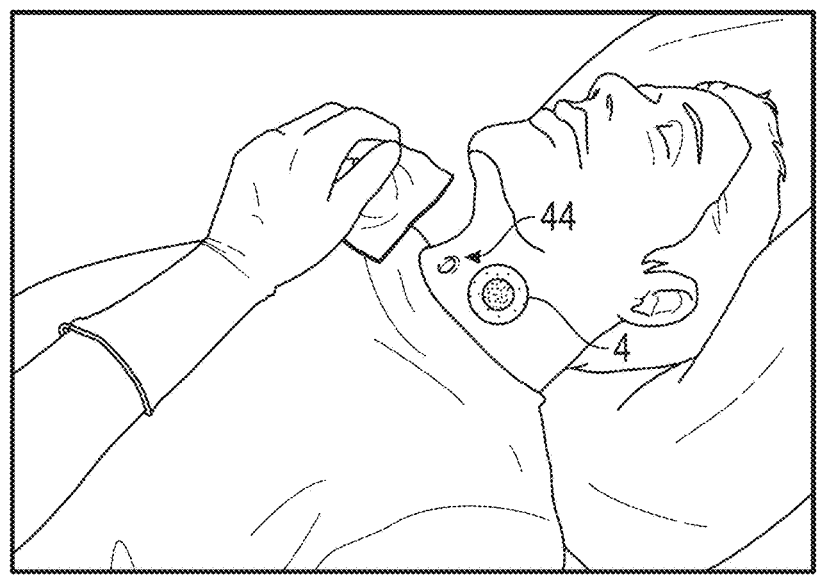
FIG. 5A shows a universal respiratory detector 4 for detecting a respiratory gas adhered to the neck skin of a tracheostomy patient with a stoma in the neck for breathing.
Figure 5B:
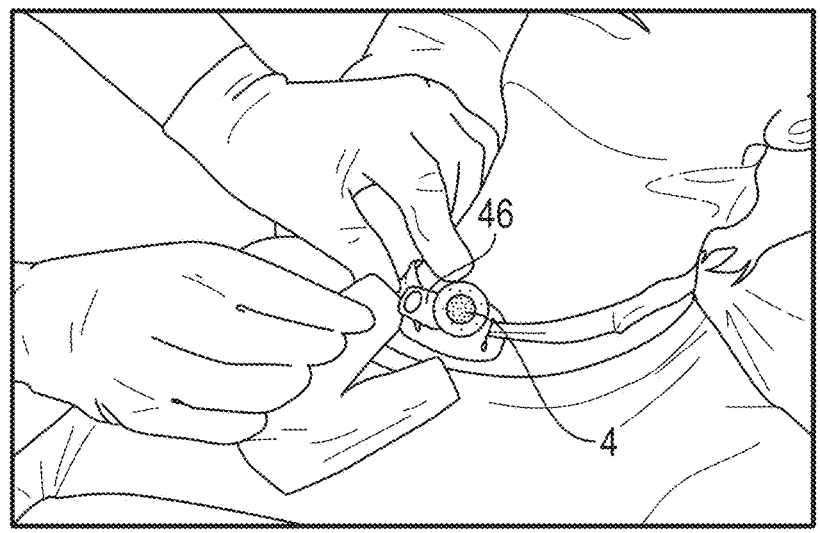
FIG. 5B shows a universal respiratory detector 4 for detecting a respiratory gas adhered to a tracheostomy tube of a tracheostomy patient with a stoma in the neck for breathing. The universal respiratory detector 4 is located close to the opening where air exchange takes place.
Figure 5C:
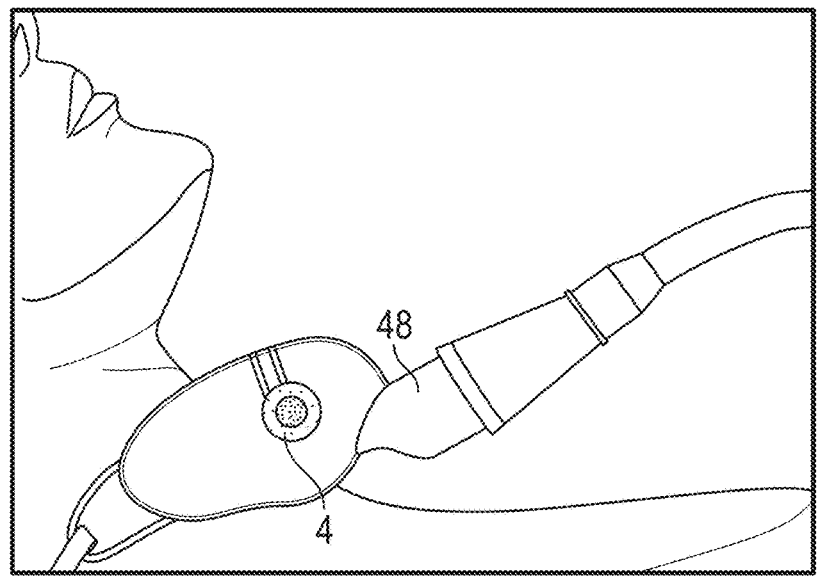
FIG. 5C shows a universal respiratory detector 4 for detecting a respiratory gas adhered to the inside of a tracheostomy mask of a tracheostomy patient with a stoma in the neck for breathing. The respiratory detector in FIG. 5C is similar to the one shown in FIG. 5B, but is adhered in the opposite orientation relative to the detector shown in FIG. 5B. The rapidly reversible visual signal of the universal respiratory detector that responds to the presence or absence of the respiratory gas is readily visible to a caregiver or health care provider.

FIG. 5A shows the universal respiratory detector 4 for detecting a respiratory gas adhered to the neck skin of a tracheostomy patient with a stoma 44 in the neck for breathing. FIG. 5B shows the universal respiratory detector 4 for detecting a respiratory gas adhered to a tracheostomy tube 46 of a tracheostomy patient with a stoma 44 in the neck for breathing. The universal respiratory detector 4 is located close to the opening where air exchange takes place. FIG. 5C shows a universal respiratory detector 4 for detecting a respiratory gas adhered to the inside of a tracheostomy mask 48 of a tracheostomy patient with a stoma in the neck for breathing. The respiratory detector in FIG. 5C is similar to the one shown in FIG. 5B, but is adhered in the opposite orientation relative to the detector shown in FIG. 5B. The rapidly reversible visual signal of the universal respiratory detector that responds to the presence or absence of the respiratory gas is readily visible to a caregiver or health care provider.

Figures 6A, 6B:
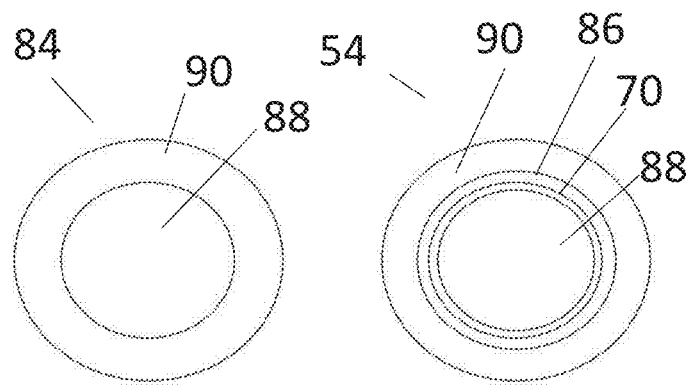
FIG. 6A-FIG. 6C illustrate different views of a universal respiratory detector with a visual indicator visible from either side and an adhesive ring serving multiple purposes.
Figure 6C:
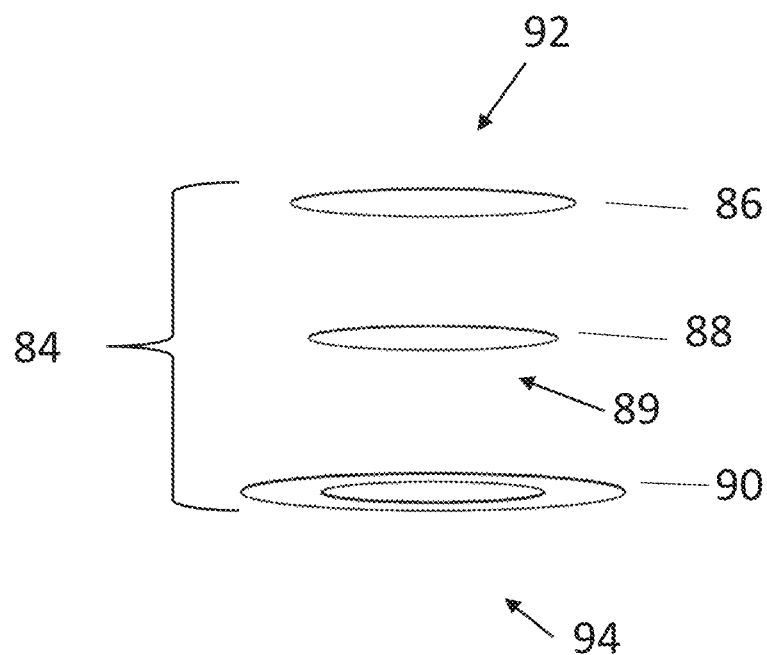

A universal respiratory detector can include multiple layers, such as 2 layers, 3 layers, 4 layers, 5 layers or more than 5 layers. Layers may be different from each other (unique) or may be the same (duplicated, and a duplicated layer may be in the same or opposite orientation). FIG. 6A-FIG. 6C illustrate different views of a universal respiratory detector 84 with multiple layers and a visual indicator visible from either side. The universal respiratory detector 84 has an adhesive ring serving multiple purposes. FIG. 6A shows a top view of the universal respiratory detector. For clarity, the transparent cover 86 on the top has been omitted from this view. Visual indicator on the bottom of backing on respiratory indictor 88 is visible from the top through the transparent or translucent backing on respiratory indictor 88. FIG. 6B shows a top view of the universal respiratory detector including the clear film 86 on top. The middle circles show areas of overlap of layers. The thin ring 70 represents the overlap of respiratory indictor 88 and adhesive layer 90. FIG. 6C shows an exploded view of the universal respiratory detector 84 and how the differing diameters of the different layers work together to create a versatile and easy to manufacture detector. The universal respiratory detector 84 has a respiratory sensor 88 configured to respond to a respiratory gas and to display a visual signal based on the response, a first cover 86 on a detector first (or top) side 92 and an adhesive layer 90 on a detector second (or bottom) side 94, opposite to the first side 92. The respiratory sensor 88 is at least partially located between the first cover 86 and adhesive layer 90. The respiratory sensor 88, and in particular a color of the respiratory sensor 88, is visible from both the sensor first side 92 and the sensor second side 94. As explained above (and with reference to FIGS. 1A-4B) the universal respiratory detector 84 can be mounted in either a first orientation or a second ("flipped over") orientation and the color of the respiratory sensor 88 can be visualized and assessed/monitored by an individual from either (or both) sides. The cover 86 can be transparent or translucent and the respiratory sensor 88 can be viewed from the first side 92. The adhesive layer 90 includes an adhesive ring or "frame" and a central open region in the center of the ring or frame through which a visual indicator on respiratory sensor 88 can be viewed from the second side 94. Adhesive layer 90 has adhesive on the top side (the side facing first side 92 in FIG. 6C). In this example, adhesive layer 90 has an outer diameter larger than an outer diameter of the other layers of universal respiratory detector 84, and the adhesive layer (e.g., an outermost ring of the adhesive layer 90 can be used for attaching the universal respiratory detector 84 to a surface (which would be at the top side 92), such as to an individual's cheek or face, or the inside or outside of a mask or tent. Because of the different diameters, the adhesive of adhesive layer 90 adheres the respiratory sensor 88 and cover 86 to itself along with the excess material beyond the outer diameter of cover 86 being what adheres the detector to its final surface (cheek, mask, etc.).

A respiratory detector as described herein, such as respiratory sensor 88, includes a respiratory sensor, such as with a visual indicator. A respiratory sensor can include a backing and a visual indicator disposed on the backing. In some variations, a respiratory sensor can include a visual indicator without a backing. A backing can be useful for providing support for a visual indicator, especially for a chemical indicator. A backing can be a relatively flat layer and may have surface features such as pores or openings. A visual indicator disposed on a backing may be disposed in pores or openings in the backing and/or disposed in a coating or layer on the backing, or both. A backing may be a first side of a respiratory sensor layer and a visual indicator on the second side of the layer. A transparent or translucent backing can allow a visual indicator to be viewed through the backing, and the visual indicator can be detected from either side of the backing. In some variations, a backing may be in the middle of a respiratory sensor layer with visual indicator on both sides (e.g., first (top) side and second (opposite) side) of the backing. A backing with visual indicator on both sides may be transparent, translucent, or opaque. A universal respiratory detector may have a single respiratory sensor layer or may have two or more than two layers of respiratory sensors. A transparent or translucent backing can allow multiple respiratory sensor layers to be stacked together in a respiratory detector as the visual signal will be visible through the transparent or translucent substrate in the multiple layers. A respiratory detector with multiple layers of visual indicator may provide a stronger, brighter, or otherwise more easily detectable visual change. In some embodiments, a respiratory device may include two backings (back to back), each with visual indicator on one side. The backings may be stacked together with the indicators facing away from each other so that indicator can be viewed from either side of a detector. A universal respiratory detector may include one layer or more than one layer (two layers, three layers, four layers, five layers, six layers, or more than six layers). In some embodiments of a respiratory sensor, a visual indicator is contained within a clear film on one or both sides.

This or any detector described herein can include an indicator material, and in particular a visual indicator (colorimetric) material, for detecting a respiratory characteristic or other chemical agent and producing and displaying visual signals in response, such as a color signals. The indicator material may be configured to rapidly respond to changes, and show a reversible and detectable color change with each inhalation and exhalation. The indicator material may detect presence, absence, and/or concentration or level of a respiratory characteristic such as a respiratory gas. A visual indicator material can display different visible properties in response to the presence, absence, and/or concentration or level of a respiratory characteristic such as a respiratory gas. A visual indicator may change between at least two different colors (e.g., yellow and blue; red and blue; green and red) as the concentration of a respiratory characteristic changes during respiration. A visual indicator may change in color, amount of color or shade (e.g., along the light spectrum), especially in the visible light spectrum. The indicator material may visually indicate the presence, absence, and/or concentration or level of a respiratory characteristic in a rapidly reversible reaction. A presence, absence, and/or concentration or level of a respiratory characteristic can be assessed qualitatively or quantitatively. Presence or absence of a respiratory characteristic including of a respiratory gas may refer to relative levels, rather than absolute levels. For example, an indicator material may detect the presence of sufficient carbon dioxide in exhaled air to individual is exhaling (breathing or respiring); however, a low of level of carbon dioxide is normally present in non-respired air. The low level of carbon dioxide in non-expired air is sufficiently low and a detector may be configured to register or consider carbon dioxide as absent or undetectable (e.g., as an absence of expired carbon dioxide since the carbon dioxide present in air is not due to an individual's breathing/expiration). Thus, in practice, an absence of carbon dioxide indicate that breathing or respiring is not occurring at a sufficient level to support the individual. Exhaled gas is typically 4% to 5% carbon dioxide while air or inhaled gas is typically 0.03% to 0.04% carbon dioxide. Exhaled gas shows a 100 fold increase in the amount of carbon dioxide relative to inhaled gas (non-respired air). A qualitative or quantitative assessment of gas showing or suggesting less than about 4% to 5% carbon dioxide, such as more than 5X (e.g. 1.2% or 1.0%) lower, more than 10X lower, more than 50X lower, or more than 100X lower, or less than 1% carbon dioxide, less than 0.5% carbon dioxide, less than 0.1% carbon dioxide, or less than 0.05% carbon dioxide with an indicator material may be considered as a sufficiently low level of carbon dioxide to indicate that respiration or breath expiration is not adequately detected. It is noted that although respired air generally contains more than 4% carbon dioxide, a respiratory detector as described herein may detect less than that and respiration may be considered acceptable. For example, a respiratory detector placed on an inner surface of an oxygen tent or a check of an individual may encounter respired air mixed with room air, resulting in a lower, but still acceptable amount of carbon dioxide, indicative of acceptable respiration for that situation. Similarly, room air or other inhalable air can contain around 21% or more oxygen, while exhaled air contains around 16%. A respiratory detector as described herein for detecting oxygen may detect more than 16% oxygen; however the individual may be respiring. Detection may be calibrated by considering the difference or cycling behavior of the indicator, rather than by absolute signal, such as absolute signal intensity or signal strength.

A respiratory indicator may be configured to change colors in response to changes in a respiratory characteristic, and in particular, to reversibly change colors as a respiratory characteristic cycles with the respiratory cycle of inhalation and exhalation. A respiratory indicator for detecting carbon dioxide can include sodium carbonate with thymol blue and glycerol or propylene glycol. Another reaction includes monoethanoloamine with metacrestol purple or thymol blue with propylene glycol.

In the broadest sense, a carbon dioxide ($CO_2$) indicator may be any convenient indicator that is capable of transducing a change in $CO_2$ concentration of a gas contacting the indicator into a detectable change, such as a detectable visual change, e.g., a colorimetric change. $CO_2$ indicators of interest include, but are not limited to, those described in U.S. Pat. Nos. 4,728,499; 4,879,999; 4,994,117; 5,005,572; 5,156,159; 5,166,075; 5,179,002; 6,436,347; 6,584,974; and U.S. Patent Application Publication No. 2006/02168282; the disclosures of which with respect to $CO_2$ indicator compositions are herein incorporated by reference.

Some variations include a long lasting $CO_2$ indicator that exhibits a dynamic, rapid response reversible $CO_2$ indication with breath-to-breath sensitivity and is storage stable. The colorimetric $CO_2$ indicator of embodiments disclosed herein changes color upon exposure to changes in concentrations of $CO_2$ found in expired air (e.g. from purple to yellow). In certain embodiments, the $CO_2$ indicator can change color, e.g. from purple to yellow, in 2.5 seconds or less, such as 2 seconds or less and including 0.75 seconds or less in response to a change in $CO_2$ concentration in a gas contacting the indicator. The indicator is sensitive to changes in $CO_2$ concentration of 3% or less, such as 2% or less, including 1% or less. At $CO_2$ concentrations of 0.05% or less, such as 0.03% or less, the indicator is a first color, while at concentrations above these amounts, the indicator is a second color. For example, in certain embodiments, the indicator exhibits the following colors at the following $CO_2$ concentrations: <0.03%, purple; 0.5% light purple; 2% brownish yellow; 5% yellow. The color change can be any of a variety of different color changes, e.g., purple to yellow, blue to yellow, red to yellow, orange to yellow, etc.

Some embodiments include the combination of various components in a concentration and ratio sufficient to provide a dynamic, rapid response reversible $CO_2$ indicator with breath-to-breath sensitivity, e.g., as described above. In one embodiment, the components of the $CO_2$ indicator include a pH sensitive indicator dye(s) and a phase transport enhancer.

pH sensitive indicator dyes of interest include, but are not limited to: bromothymol blue, phenolphthalein, thymol blue, phenol red, rosolic acid, m-nitrophenol, xylenol blue, curcumin, cresolphthalein, thymolphthalein, malachite green, N,N-dimethylaniline, and cresol dyes, e.g., bromocresol green, bromocresol purple, cresol red, m-cresol purple, etc. In certain embodiments, the pH sensitive indicator dye is a cresol dye or combination thereof, e.g., a combination of m-cresol purple and cresol red.

In addition, the pH sensitive indicator dye, another component present in the indicator described herein can be a phase transport enhancer. Phase transport enhancers contained as part of the dye solution applied to the support surface, enhance response of the dye to $CO_2$ gas as well as alter the color and visibility of the indicator. Phase transport enhancers include, but are not limited to: quaternary ammonium, phosphonium or pyridinium salts. Quaternary salts which are useful in sensors described herein have the formula (I):

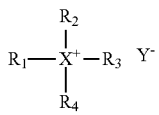

wherein:
X=N or P;
R1, R2, R3 and R4 are selected from the group consisting of C1-C16, such as C1-C12 alkyl, triphenylmethyl, phenyl, naphthyl and benzyl, C1-C4 substituted alkyl wherein the substituent is a C1-C4 alkyl or phenyl group, wherein R1, R2, R3 and R4 may be the same or different, e.g., have the same or different number of carbon atoms; and Y—is an anion selected from the group consisting of hydroxide, fluoride, chloride, bromide, iodide, carbonate and tetrafluoroborate.

Phase transport enhancers which are useful in some embodiments include, but are not limited to: tetrabutylammonium hydroxide; tetrabutylammonium chloride; tetraethylammonium bromide; tetraethylammonium p-toluenesulphonate; phenyltrimethylammonium chloride; benzyltrimethylammonium bromide; tetra-n-propylammonium bromide; benzyltriethylammonium tetrafluoroborate; n-Dodecyltrimethylammonium bromide; tetraphenylphosphonium chloride; n-Hexadecylpyridinium bromide; and (Triphenylmethyl)triphenyl phosphonium chloride.

Some embodiments can be produced by combining the various components of the indicator composition to produce a precursor indicator reagent fluid and then contacting the fluid with a suitable solid support in a manner sufficient to produce the desired indicator composition. In certain embodiments, the precursor fluid is an aqueous solution, such as a basic aqueous solution, that includes the above described pH sensitive dye and phase transport components. The basic solution has, in certain embodiments, a pH ranging from 10 to 12.5. The composition may include one or combination of pH sensitive indicator dyes. In certain embodiments, the composition includes more than one pH sensitive indicator dyes, such as 2 to 5 different dyes, e.g., 2 to 4 different dyes, including 2 to 3 different dyes, e.g., 2 different dyes. In certain embodiments, the dyes are cresol dyes, such as 2 different cresol dyes. When the composition includes two different pH sensitive indicator dyes, the pH sensitive indicator dyes can be present in a concentration ranging from 0.0001 Molar to 0.01 Molar, including about 0.002 Molar to 0.003 Molar. In certain embodiments, the dyes are m-Cresol purple and cresol red. M-cresol purple can be present in the reagent fluid in a concentration ranging from 0.001 Molar to 0.01 Molar, including about 0.002 Molar to 0.003 Molar. Cresol red sodium salt can be present in reagent fluid in a concentration ranging from 0.0001 Molar to 0.001 Molar, including about 0.002 Molar to 0.003 Molar. The concentration of phase transport enhancer may vary. In certain embodiments, the amount of phase transport enhancer present in the reagent fluid ranges from 0.001 Molar to 0.02 Molar, such as from 0.005 Molar to 0.01 Molar.

Following preparation of the precursor fluid, the methods can include contacting the fluid with a solid support, and then removing excess fluid from the solid support to produce the indicator. Any convenient solid support may be employed. In certain embodiments, the solid support is a flexible solid support (e.g. a cellulosic material), e.g., paper. In certain embodiments, the solid support may be a filter paper, e.g., having a porosity ranging from 1 μm to about 60 μm, such as from 20 μm to about 30 μm. The solid support can be a material dimensioned to fit on skin and or inside an oxygen delivery device, such as described herein. The support of the $CO_2$ indicator can be shaped into any desired configuration, including but not limited to: circular or spiral strips, a sphere or portion of a sphere, a propeller, an accordion shape, etc. The support of the indicator can further comprise a pattern, and/or can have perforations, as described in the above embodiments.

The above described indicators can be used in any of a number of different respiratory detectors. In certain embodiments, the indicators are employed with respiratory detectors that do not include a sterilization barrier, as the indicator of such embodiments can survive the sterilization, e.g., EtO, process.

Returning to FIG. 6A-FIG. 6C, the adhesive layer 90 can be in the form of a ring or frame surrounding an open center portion. The open center portion allows respired air to contact the respiratory sensor 88 during detector use. The respiratory sensor 88 is visible through the center or "picture" portion of the ring or frame such as to an individual assessing and/or monitoring the individual's respiratory status. Adhesive layer 90 may include a substrate with one or more adhesive compounds on a top side of the adhesive layer (e.g., the side facing the respiratory sensor 88 and sensor second side 94). The adhesive layer 90 may adhere to an outer portion of respiratory sensor 88, as well as to the bottom of cover 86 and may hold the adhesive layer 90, respiratory sensor 88, and cover 86 together. An adhesive in adhesive layer 90 that contacts the respiratory sensor 88 may be an adhesive that does not interfere with or only minimally interferes with visual indicator performance. Examples of adhesives that may be used in adhesive layer 90 include no or low off-gassing adhesives such a silicone adhesive, a low volatile organic compound adhesive (low VOC) such as a low VOC acrylic. In some variations, the adhesive layer 90 can additionally or instead have an adhesive surface facing the sensor first side 92 for attachment of the respiratory indicator to a surface at the sensor first side 92. The adhesive portion on adhesive layer 90 may cover part or all of the top side of adhesive layer 90. In some variations, the adhesive layer 90 may not cover the entire top side of adhesive layer 90. Adhesive layer 90 may take other forms, such as a discontinuous adhesive (e.g., an array of small circles or squares of adhesive) or a 2-dimensional spiral form with an adhesive spiral and open (non-adhesive) areas, or another form, and the respiratory sensor 88 may be visible through the discontinuities or open areas in the adhesive. In some variations, the adhesive layer 90 includes an air permeable or breathable membrane in part or all of the center portion. A breathable membrane allows expired air from the individual to flow through and contact respiratory sensor 88, and may provide protection for the otherwise exposed (bottom) surface of respiratory sensor 88. In some variations, an adhesive layer, such as adhesive layer 90, may cover substantially an entire sensor second surface. An adhesive that is clear (or translucent) may be well suited to cover an entire sensor first surface as a signal (visual signal) from a respiratory indicator could be visualized through a clear or translucent adhesive surface. In some variations, an adhesive may be opaque. Although FIG. 6A-FIG. 6C show the adhesive layer 90 adjacent the respiratory sensor 88 in the respiratory detector 84, in some variations, an adhesive could be provided separately from the respiratory indicator and attached to a respiratory detector during application of the respiratory detector to an individual with the adhesive. For example, an adhesive could be configured (and packaged) as a separate layer (with a backing) or a gel that may be applied/attached to the rest of respiratory sensor 84 (cover 86 and respiratory sensor 88). In some variations, a detector may have an adhesive on adhesive layer such as adhesive layer 90 in FIG. 6A-FIG. 6C for attaching respiratory sensor 88 to a cover 86. In some variations, adhesive layer 90 may attach a detector to an individual. In some variations, a detector may have an adhesive, such as on the top of cover 86 for attaching a detector to an individual, in addition to or instead of adhesive on adhesive layer 90. A respiratory detector placed on and adhered to facial skin or an oxygen delivery device may stay in place on the skin or delivery device for a period of time (minutes, hours, days, weeks) and then be removed and thus a respiratory detector may need to be removable. In some cases, a respiratory detector may be removed and replaced one time or more than one time by a fresh/new additional respiratory detector (s) placed on facial skin or an oxygen delivery. These additional respiratory detector(s) may also stay in place for a period of time (minutes, hours, days, weeks). Ease of applying and replacing the respiratory detector may be important. Other detector characteristics that may be of interest for a respiratory detector described herein include stability, ease of use, conformability, flexibility, ability to adhere, comfort, skin irritability, and comfort of removal. In some embodiments, a visual indicator is configured to reversibly change color when a respiratory gas parameter changes and to display the color change for a period of time lasting at least 10 minutes, at least one hour, at least ten hours, at least one day, at least three days, at least one week, or at least two weeks or between these amounts. A respiratory detector may be configured for conformability and flexibility for conforming to uneven facial skin or an irregularly shaped oxygen delivery device, such as an oxygen cannula and for flexibility to stay in place and be comfortable to wear after being placed. As indicated above, it may be desirable to place a respiratory detector close to where breath is exhaled, such as on facial skin between the nose and mouth, areas which may be irregular or flat and may have either or both convex and concave areas. A detector that can sufficiently conform for mounting and is flexible as the person speaks, laughs, or otherwise moves their face may be desirable. It can be very difficult to get anything to adhere to skin, and especially to adhere to facial skin. Facial skin is delicate, sensitive, and prone to damage, irritation, skin rashes, and acne and an adhesive of a respiratory indicator (as well as other parts of a respiratory indicator) may be hypoallergenic and non-irritating for a period of hours or days. An optimal adhesive for adhering a respiratory indicator to an oxygen delivery device may not be the optimal adhesive for adhering a respiratory indicator to an individual's facial skin and vice versa. Facial skin has a low surface energy in the best of circumstances, making it difficult to adhere an adhesive to it. Different individuals also have a wide range of skin conditions that affect the ability of an adhesive to adhere a respiratory indicator to facial skin and a universal respiratory detector may be configured to provide the best adhesion for a number of circumstances. For example, individuals have different sebum levels, dryness, sweating, and facial hair. The presence of any face cream, ointment, or sunscreen on facial skin affects adhesion and respiratory detector adhesion to the facial skin. It can be very difficult to get anything to adhere to facial skin and painful or damaging to the skin to remove it, even on healthy skin.

As indicated above, other adhesive characteristics that may be of interest for a respiratory detector described herein are ease and comfort of removal. Concerns about skin trauma during adhesive removal may include concerns about skin tears and skin stripping. Facial skin in younger patients such as babies as well as in elderly patients may be particularly sensitive to skin trauma. As skin ages, its dermal thickness decreases, leading to a thinning of the skin, making the skin more vulnerable to damage. Aging skin predisposes an individual to skin tears, such as painful and unsightly separation of the epidermis layer of the skin from the underlying dermal layer. These factors make atraumatic removal of an adhesive in a respiratory detector more challenging. Ease of wear of a respiratory detector, comfort during removal of a respiratory detector, and ensuring the respiratory detector factor stays in place during use may be considered when choosing an adhesive. For example, if the degree of adhesion is too low, the respiratory sensor might not reliably stay in place. If the degree of adhesion is too high, the respiratory sensor may be difficult to remove and removal may cause damage to facial skin or an oxygen delivery device. An adhesive for adhering a respiratory device to skin or an oxygen delivery device and for gentle removal may include the adhesive and detector releasing cleanly from skin or device, leaving the skin area intact and leaving behind no or little residue during removal. Gentle removal from skin may also include minimal or no pain during removal. An adhesive may be configured to be atraumatic during use and removal. Adhesive performance for a respiratory sensor may balance different characteristics. Adhesive performance can be characterized in part by adhesive tack, peel, and/or shear. Tack is a measure of how quickly a bond is formed between two surfaces, such as between an adhesive and a surface (e.g., skin or oxygen delivery device), and may be used to refer to pressure sensitive adhesives. In some embodiments, an adhesive is configured to be tacky or non-tacky at room temperature. To assay tack, two surfaces are brought together briefly under light pressure, then pulled apart. The more force needed to separate them, the higher the tack. Lower tack may allow an adhesive to be repositioned. Another characteristic of an adhesive is peel. Peel is a measure of the force needed to break a bond between the adhesive and the surface (e.g., skin or oxygen delivery device) to which it has been applied. A peel test to assay peel can be performed. In peel testing, an adhesive tape is applied to a surface, allowed to sit, and then pulled away. Peel angle or direction, application pressure and the length of time the surfaces stay bonded may be defined, such as in ASTM D330D standard test method to measure peel adhesion strength in a pressure sensitive tape. In some examples, an adhesive is allowed to sit on a surface at least one hour, at least two hours, at least three hours, at least five hours, at least ten hours, at least twenty-four hours, at least forty eight hours or at least sixty hours or less than sixty hours, less than forty eight hours, less than twenty four hours, less than ten hours, less than five hours, less than four hours, less than three hours, less than two hours, less than one hour, or any amount of time between these (at least ten hours and less than forty eight hours, etc.). Another characteristic of an adhesive is shear. Shear refers to one surface sliding over another. In a shear test, a sample is mounted vertically and has a weight attached. The time is takes for the sample to slip off the substrate shows the durability of the bond. An adhesive may include sufficient tackiness to adhere to a device and/or skin and good shear and peel character to remain on the device and/or skin and be readily removable from a device and/or skin. An adhesive for a respiratory detector may be or include acrylics, hydrocolloids, hydrogels, rubber-based adhesives, or polyurethane based adhesives. Examples of adhesive polymers for an adhesive include polysiloxane or silicone (BIO-PSA from Dow Corning®), polyisobutene (Oppanol®), a syrene-isoprene-styrene copolymer (JSR-SIS), or an acrylic polymer (Duro-Tak). A substrate for an adhesive may be a sheet or film, such a foam, polymer, plastic, or polyester resin (mylar) sheet or film. A substrate may be clear, translucent, or opaque. In some examples, a diameter (outer diameter) or other longest dimension (e.g., a length or diagonal of a non-circular shaped layer) of an adhesive layer may be about 1 inch, or less than 2 inches, less than 1.5 inches, less than 1 inch or less than 0.5 inch or less than 0.25 inches or at least 0.5 inches, at least 1.0 inches, at least 1.5 inches or at least 2.0 inches or between these amounts (e.g., at least 0.5 inches and less than 1 inch, at least 0.5 inches and less than 1.5 inches).

In some variations, the sensor first side may have a cover over at least the center ("picture") portion of the ring or frame of adhesive layer 90 instead or in addition to the first cover. As indicated above, a universal respiratory detector first side may have a cover over the center or "picture" portion of the ring or frame of adhesive layer 90 instead or in addition to the first cover. In some embodiments, a cover is a film. In some variations, a respiratory sensor does not have a cover.

Figure 7:
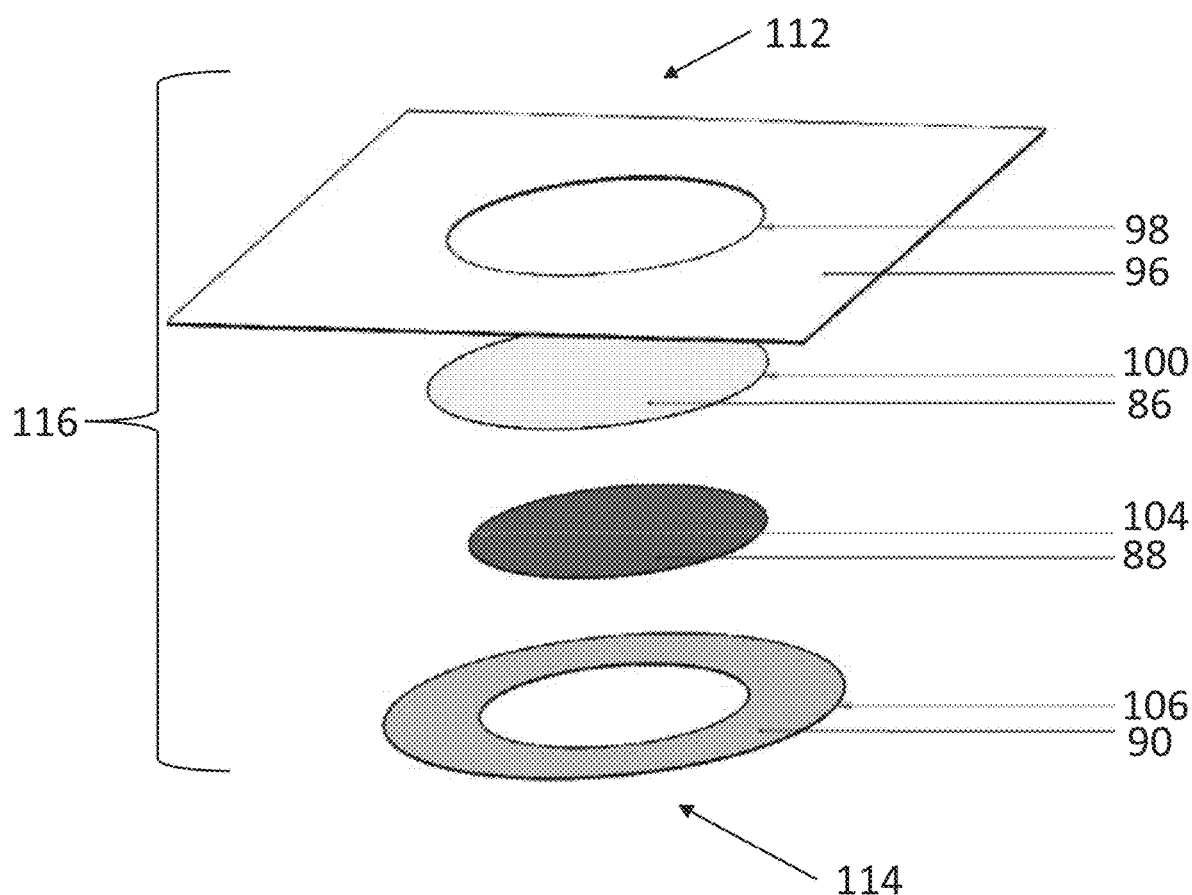
FIG. 7 shows an exploded view of a multilayered universal respiratory detector with an adhesive ring and a transparent backing.

FIG. 7 shows an exploded view of another respiratory detector, universal respiratory detector 116. Similar to as described above for universal respiratory detector 84 in FIG. 6A-FIG. 6C, the universal respiratory detector 116 shown in FIG. 7 has a respiratory sensor 88 configured to respond to a respiratory parameter (e.g., a gas, such as $CO_2$) and to display a visual signal based on the response. The universal respiratory detector 116 has an adhesive layer 90 on a sensor second side 114, and a first cover 86 and respiratory sensor 116 includes release liner 96 on detector first side 112. As indicated above, respiratory sensor 88 and any other respiratory sensor described herein may have a backing and a visual indicator on the backing. A backing may be a porous material and the backing may be configured to allow a visual indicator to penetrate the pores or otherwise hold a visual indicator during detector manufacture, storage, and use. Pores of a backing may be irregular (e.g., in a polymer) or regular (e.g., laser drilled). Pores may have an average pore size of around 0.65 um, or from about 0.45 um to 0.8 um, or from about 0.1 um to about 2 um, or from about 0.03 um to about 5.0 um or any size between these. In some variations and as indicated elsewhere herein, average pore size may be larger than 5 um. A visual indicator may be configured to indicate/change with each breath such as within 3 seconds, within 2 seconds, within 1 second, or within 0.5 seconds. A backing may be a polymer such as polyethersulfone, polysulfone, or polyphenylene sulfone. A backing may be clear or translucent such that a visual indicator can be visualized through the backing (e.g., the visual indicator can be assessed from both sides of the universal respiratory detector 94) or may be opaque. Visual indicators, such as indicated elsewhere herein, can be adhered or attached to a backing, such as using pad printing. Visual indicators can be printed to the bottom side (e.g., facing second side 114) of respiratory sensor 88 by pad printing. In some examples, visual indicators printed on the second side of a respiratory sensor, such as respiratory sensor 88, contact adhesive, such as on an adhesive layer 90 when the respiratory sensor 88 and adhesive layer 90 are joined together. In some examples, visual indicators are printed so that they do not contact adhesive when the respiratory sensor 88 and adhesive layer 90 are joined together. Contact of visual indicator by an adhesive may have a detrimental effect on a visual indicator, such as reducing shelf life or visual indicator efficacy. Preventing or minimizing contact between visual indicators and adhesive may improve visual indicator life. A solution including visual indicator, plasticizer, and isopropyl alcohol may be placed onto a backing (e.g., polyethersulfone membrane) and the visual indicator cured onto the substrate and isopropyl alcohol flashed off by heating at 80° C. for 10 min or 90° C. for 5 min. Respiratory sensor 88 also includes first cover 86. First cover 86 may be laminated to the top side of respiratory sensor 88 and the top side of respiratory sensor 88 may be sealed by first cover 86 to protect the visual indicator 88 and increase sensor durability. First cover 86 may protect the visual indicator from humidity and prevent oxidation. In some examples, the visual indicator is configured and protected to provide visual indication for at least one day, at least two days, at least three days, or at least four days of use. In some examples, a universal respiratory detector described herein such as universal respiratory detector 84 is protected on its edges by a coating, film, or bead.

Figure 8A:
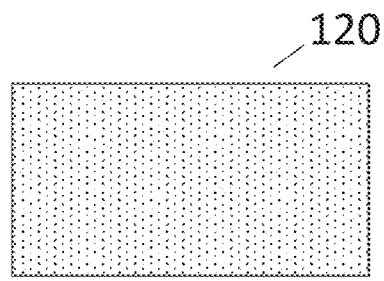
FIG. 8A-FIG. 8H show examples of variously shaped universal respiratory detectors.
Figure 8B:
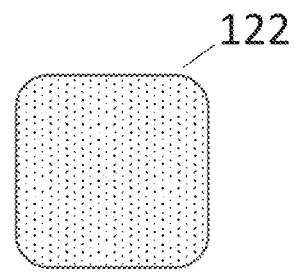
Figure 8C:
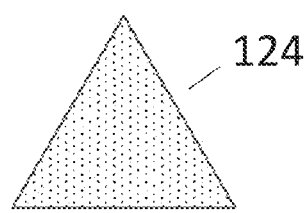
Figure 8D:
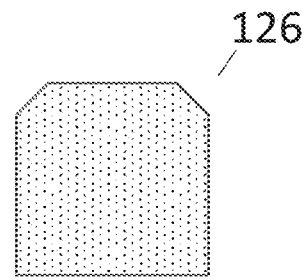
Figure 8E:
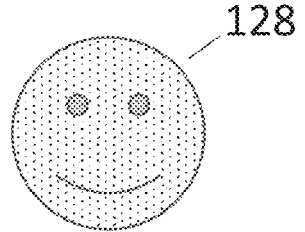
Figure 8F:
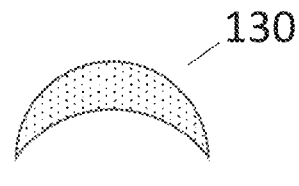
Figure 8G:
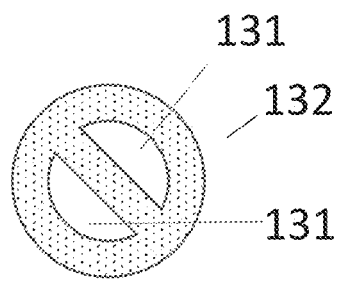
Figure 8H:
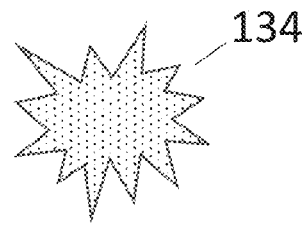
Figure 10:
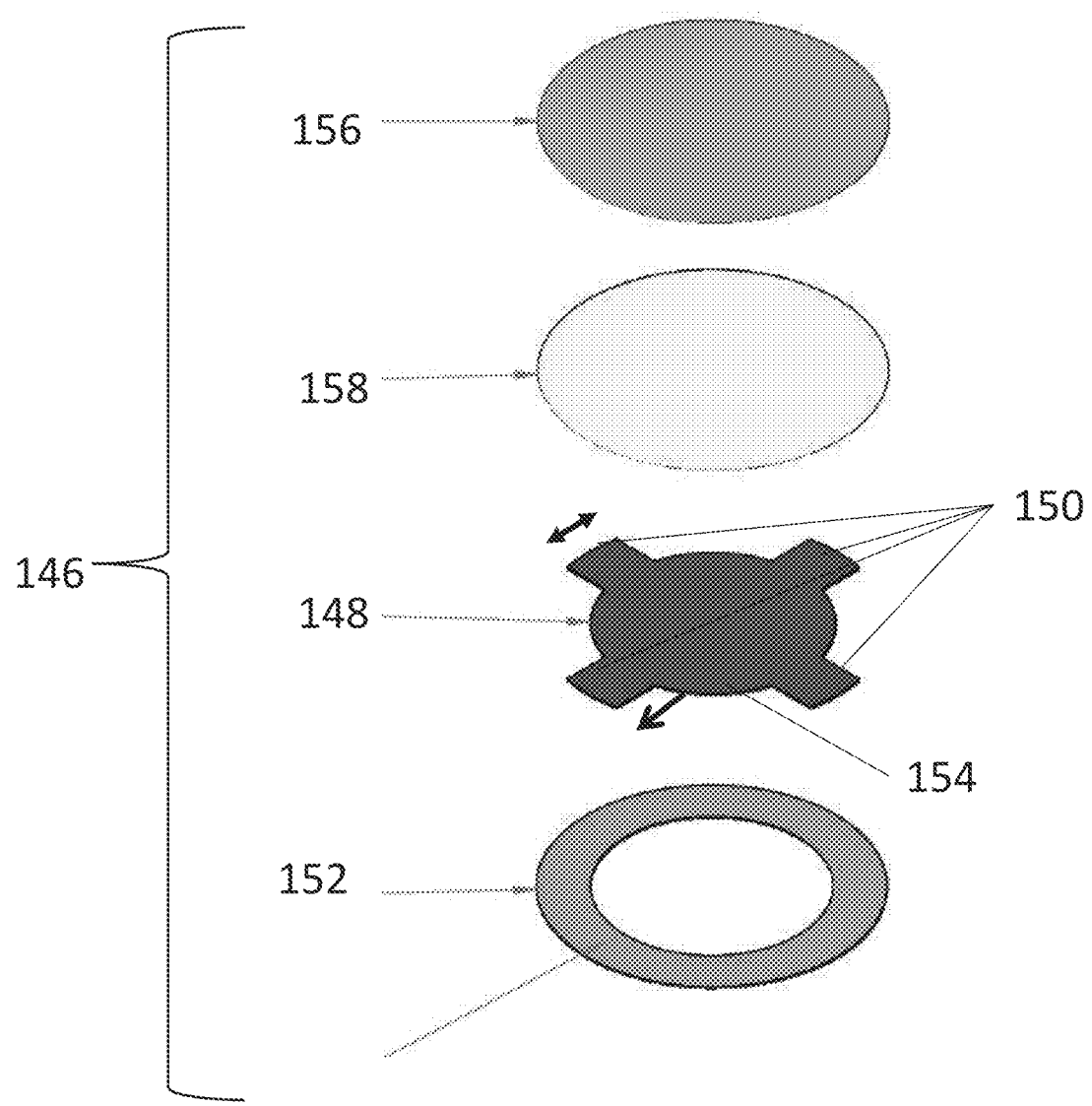
FIG. 10 shows an exploded view of a multilayered universal respiratory detector with an indicator with tabs.

FIG. 7 also shows respiratory sensor 88 includes a release liner 96. A release liner, such as release liner 96, can be a thin, removable layer that protects the universal respiratory detector 116. In particular, release liner 96 may protect adhesive layer 90 and maintain its adhesive integrity prior to detector mounting, keeping it out of contact with air, dirt, or other objects and preventing it from premature adhering. In some variations, a respiratory detector may have a second release liner for a second adhesive layer or second adhesive side. A release liner, such as release liner 96, is removed prior to universal respiratory detector 94 mounting and use. Steps in methods of use of a release liner may include protecting a universal respiratory detector with a release liner, and removing or separating the release liner from rest of the universal respiratory detector. A release liner may be larger or longer (in diameter, width, and/or length) than another part of a universal respiratory detector, or may be smaller or shorter (in diameter, width, and/or length) than another part of a universal respiratory detector, or may be the same size as another part of a universal respiratory detector. In some variations, a universal respiratory detector may have a release liner on the sensor first side instead of, or in addition to, the release liner on the sensor second side 114 and a respiratory detector may have zero, one, two, or more release liners. A release liner may be a substrate coated on one or both sides with a release agent, configured to separate the release liner from adhesive (and/or other material) of the respiratory sensor. A release liner can be a paper, plastic, fluoropolymer, polyethylene film or layer coated with silicone. A release liner can be smooth or textured with release properties to allow for adhesion of the adhesive while permitting clean separation from the adhesive during respiratory sensor application to a surface. A release liner may include one or more cut features or extensions, such as a cutout or hole in the middle as shown in FIG. 7 or a partial line cut(s) or a tab extension that may aid is respiratory sensor application and/or removal. In some examples, a diameter (inner diameter) or other dimension (e.g., diagonal of a rectangular shaped layer) of an internal opening on release layer may be less than 2 inches, less than 1.5 inches, less than 1 inch or less than 0.5 inch or at least 0.5 inches, at least 1.0 inches, at least 1.5 inches or at least 2.0 inches or between these amounts (e.g., at least 0.5 inches and less than 1 inch, at least 0.5 inches and less than 1.5 inches), such as at least 0.5 inches and less than 1.0 inches, at least 0.5 inches and less than 1.5 inches. A release liner may be sized to extend beyond the perimeter of the rest of the respiratory sensor, such as by at least 0.25 inches, at least 0.5 inches, or at least 1 inch. Another layer may also or instead have a tab or ring extension. A cut feature or extension may aid in detector placement or aid in release liner separation from the adhesive or another part of the universal respiratory detector. A cut feature or extension such as in an adhesive layer and a detector chemical may aid in minimizing contact between the adhesive and the detector chemical. Such minimization may be advantageous, for example, if an adhesive has a detrimental effect on the stability of a detector chemical. A tab may be rectangular, V-shaped (narrow near the body), inverted V-shaped (wide near the body), rounded, or another shape. A tab may be flat and may have the same or similar thickness as the layer to which it is connected. A tab may be flexible or inflexible. As indicated above, a respiratory detector may be circular or ovoid. In these and other embodiments, the universal respiratory detectors has no sharp edges or corners. A circle can be the most efficient and stable shape since sensor degradation can start from the outer edges and move inward. Other shapes are also contemplated for a respiratory detectors. FIG. 8A shows a rectangular universal respiratory detector 120. FIG. 8B shows a rounded square rectangular universal respiratory detector 122. FIG. 8C shows a triangular rectangular universal respiratory detector 124. FIG. 8D shows a cut rectangular universal respiratory detector 126. FIG. 8E shows a decorated rectangular universal respiratory detector 128 with graphics. FIG. 8F shows a crescent shaped rectangular universal respiratory detector 130. FIG. 8G shows a split rectangular universal respiratory detector 132 with two parts 131. Parts 131 may contain adhesive, indicator, or any respiratory detector material as described herein. FIG. 8H shows a starburst shaped 134. FIG. 10 shows an exploded view of a universal respiratory detector 146 similar to as described above but with respiratory sensor 148 with four tabs 150. When adhesive layer 152 is in place over respiratory sensor 148, the amount of contact between adhesive layer 152 and respiratory sensor 148 can be minimized. For example, the contact may be limited to the region between a tab and the adhesive layer and/or a thin ring 154 around the outer circumference of the respiratory sensor 148. A respiratory sensor 148 may have three, four, or five tabs (or may have another number of tabs such as one tab, two tabs, or more than five tabs or no tabs). The tabs (or extent of respiratory sensor 148 if no tabs) may extend so that the outermost dimension size of the respiratory sensor 148 is the same outermost dimension size (e.g., circumference) as some or all of the other layers in a respiratory sensor. Having the same outermost dimensions for some or all of the layers may aid in manufacturing: a series of layers of materials may be layered together and respiratory sensors, such as respiratory sensor 146, may be punched out from the layers. A plurality of detectors can be manufactured together in sheet or web/roll form. In another embodiment, the various layers in a respiratory sensor, such as respiratory sensor 146, can be separately shaped (punched or cut), and then lined up after shaping (punching or cutting) to form an assembled respiratory sensor either separately or in groups in which a number of detectors are simultaneously assembled. The tabs may extend beyond the circumference of the main body (e.g., outwardly from ring 154 as indicated by the arrow in FIG. 10 by not more than 0.1 inches, not more than 0.2 inches, not more than 0.3 inches, not more than 0.4 inches, or more than 0.4 inches. The tabs may be not more than 0.1 inches in width as indicated by the double arrow in FIG. 10, not more than 0.2 inches, not more than 0.3 inches, not more than 0.4 inches, or more than 0.4 inches in width. These extension and width dimensions may also apply to other shaped tabs, such as to the biggest, smallest, or average size of a V shaped tab.

A respiratory sensor, such as universal respiratory detector 4, 6, 116, 120, 122, 124, 126, 128, 130, 132, 134 may be configured as stickers (e.g., be flexible, pliable, and thin and able to conform to a surface, able to adhere to a surface upon contact or minimal applied pressure) and may be configured as removable stickers. Such sensors may be about 0.01 inches thick, such as between 0.005 inches and 0.05 inches or between 0.001 inches and 0.1 inches. Each layer may be thin and flexible. Release liner 156 in FIG. 10 may be about 0.002 inches thick, such as between 0.0005 inches and 0.008 inches or between 0.0002 inches and 0.02 inches or between 0.001 inches and 0.1 inches. Cover 158 in FIG. 10 may be about 0.002 inches thick, such as between 0.0005 inches and 0.008 inches or between 0.0002 inches and 0.02 inches or between 0.001 inches and 0.1 inches. Cover 158 in FIG. 10 may be about 0.002 inches thick, such as between 0.0005 inches and 0.008 inches or between 0.0002 inches and 0.02 inches or between 0.001 inches and 0.1 inches. Respirator indicator 148, which may include a backing with a visual indicator may be about 0.004 inches thick, such as between 0.0004 inches and 0.04 inches or between 0.0002 inches and 0.02 inches. In some variations, a respiratory sensor may have a rigid housing. A universal respiratory detector as described herein may be conformable to many types of oxygen delivery systems (e.g., facemask, nasal cannula, continuous positive airway pressure machines (CPAP), tracheostomy collar, oxygen tent). A universal respiratory detector may be a single use, disposable, latex free, non-metallic, magnetic resonance imaging (MRI) safe and/or computerized tomography (CT) safe. A universal respiratory detector as described herein may have sufficient visibility to be visible from at least 5 feet away or at least 10 feet away. Once manufactured, a universal respiratory detector as described herein can be packaged in an airtight packet (e.g., mylar). The entire packet may be small (e.g., less than 1.5 inches or less than 1 inch on each side and less than 0.1 inches, or less than 0.05 inches thick. Some embodiments of a respiratory detector include a backing, an adhesive layer, a visual indicator, and an opaque surrounding layer. An opaque surrounding layer may contain printed graphics such as instructions or decoration.

Examples

Example 1: Universal respiratory detectors manufactured as described herein were subjected to accelerated stability testing to quickly and accurately measure and estimate the stability of universal respiratory detectors. The universal respiratory detectors were subject to extreme conditions that increase the rate of chemical and/or physical degradation that would occur under normal storage conditions. Universal respiratory detectors were manufactured as shown in FIG. 10 with a (top) release liner layer, a clear polyester layer with adhesive on the top surface, a visual indicator on the topside of a polyethersulfone backing, and a (bottom) polyester with a low off-gassing acrylic adhesive on top and a cutout in the middle. The sensors were sealed in a mylar foil package, heat sealed, and artificially aged in an oven at 55° C. After 18 days at 55° C., which equates to 6 months of real time, the sensors showed no signs of degradation.

Example 2: Universal respiratory detectors manufactured as described herein were subjected to accelerated stability testing to quickly and accurately measure and estimate the stability of universal respiratory detectors. The universal respiratory detectors were subject to extreme conditions that increase the rate of chemical and/or physical degradation that would occur under normal storage conditions. Universal respiratory detectors were manufactured as shown in FIG. 10 with a (top) release liner layer, a clear polyester layer with adhesive on the top surface, a respiratory indicator layer on the topside of a polyethersulfone backing, and a (bottom) polyester with a silicone adhesive on top and a cutout in the middle. The sensors were sealed in a mylar foil package, heat sealed, and artificially aged in an oven at 55° C. After 36 days at 55° C., which equates to 12 months of real time, the sensors showed no signs of degradation.

Example 3: Universal respiratory detectors manufactured as described herein were subjected to accelerated stability testing to quickly and accurately measure and estimate the stability of universal respiratory detectors during universal respiratory detector use. The universal respiratory detectors were subject to extreme conditions that increase the rate of chemical and/or physical degradation that would occur under normal storage conditions. Universal respiratory detectors were manufactured as shown in FIG. 10 with a (top) release liner layer, a clear polyester layer with adhesive on the top surface, a visual indicator layer on the topside of a polyethersulfone backing, and a (bottom) polyester with an adhesive on top and a cutout in the middle. The sensors were not sealed in packaging. The sensors were left open to the atmosphere (air). The sensors were artificially aged in an oven at 55° C. After 10 days at 55° C., which equates to 3 months of real time, the samples showed a 50% reduction in efficiency: 50% of the chemistry indicator was permanently yellow and 50% would still change from blue to yellow and back. The pattern of degradation was typically in the shape of a circle/oval, in which the degradation moved from the outer edges inward (e.g., degradation was noted nearer the interface of the respiratory sensor layer (chemical) with the adhesive, suggesting that adhesive may have a negative impact on respiratory indicator (chemical) stability.

Example 4: Polyethersulfone membranes were overlaid with solution of visual indicator, plasticizer, and isopropyl alcohol. Membranes were heated from 80° C. to 180° C. and visually assessed. Membranes heated at 80° C. for 10 minutes or 90° C. for 5 min had acceptable color. Membranes heated at 180° C. for 5 min were unacceptable.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A universal respiratory detector for detecting a respiratory gas and displaying a respiratory status based on the gas, the respiratory detector comprising:
    a first side and a second side opposite the first side;
    a cover layer, wherein the cover layer covers at least part of a backing;
    a respiratory sensor layer comprising the backing and a visual indicator on the backing, the visual indicator configured to reversibly change color when a respiratory gas parameter changes and to display the color change, wherein the color change is visible from both the first side and the second side; and
    a biocompatible adhesive on the cover layer and a release liner on top of the biocompatible adhesive,
    wherein the universal respiratory detector is a sticker, and further wherein the detector is configured to conform to a curved or variable surface contour of an oxygen delivery device or a face of a user and configured to flex and move together with movement of the oxygen delivery device or the face of the user.

2. The universal respiratory detector of claim 1, wherein the universal respiratory detector is substantially circular or ovoid in shape.

3. The universal respiratory detector of claim 1, wherein the universal respiratory detector has no sharp edges or corners.

4. The universal respiratory detector of claim 1, wherein the release liner comprises paper, plastic, fluoropolymer, polyethylene film, or a layer coated with silicone.

5. The universal respiratory detector of claim 1, wherein the release liner comprises a substrate having a release agent, wherein the release agent is configured to aid in separating the release liner from the adhesive.

6. The universal respiratory detector of claim 1, wherein the detector comprises a low or no off-gassing adhesive ring on the second side, wherein the adhesive ring adheres the respiratory sensor layer to the cover layer.

7. The universal respiratory detector of claim 6, wherein the adhesive ring has a transparent or translucent region in a center portion therein.

8. The universal respiratory detector of claim 1, wherein the backing comprises polyethersulfone, polysulfone, or polyphenylene sulfone.

9. The universal respiratory detector of claim 1, wherein the universal respiratory detector has a longest dimension of less than 1 inch.

10. The universal respiratory detector of claim 1, wherein the visual indicator is configured to reversibly change color in response to carbon dioxide.

11. The universal respiratory detector of claim 1, wherein the universal respiratory detector is biocompatible.

12. The universal respiratory detector of claim 1, wherein the visual indicator is configured to reversibly change color when a respiratory gas parameter changes and to display the color changes for a period of time lasting at least one hour.

13. The universal respiratory detector of claim 1, wherein the visual indicator is configured to reversibly change color when a respiratory gas parameter changes and to display the color changes for a period of time lasting at least ten hours.

14. The universal respiratory detector of claim 1, wherein the detector is non-metallic, latex free, and configured to be single use and disposable.

15. A universal respiratory detector for detecting a respiratory gas and displaying a respiratory status based on the gas, the respiratory detector comprising:
   a first side and a second side opposite the first side;
   a cover layer, wherein the cover layer covers at least part of a backing; and
   a respiratory sensor layer comprising the backing and a visual indicator on the backing, the visual indicator configured to reversibly change color when a respiratory gas parameter changes and to display the color change, wherein the color change is visible from both the first side and the second side,
   wherein the universal respiratory detector is a sticker, and further wherein the detector is configured to conform to a curved or variable surface contour of an oxygen delivery device or a face of a user and configured to flex and move together with movement of the oxygen delivery device or the face of the user,
   wherein the universal respiratory detector comprises a maximum thickness of less than 0.1 inches.

16. The universal respiratory detector of claim 15, wherein the respiratory indicator is configured to reversibly change color in response to carbon dioxide and to display the color changes for a period of time lasting at least ten hours, further wherein the detector comprises a low or no off-gassing adhesive ring on the second side adhering the respiratory sensor layer to the cover layer, and wherein the adhesive ring has a transparent or translucent region in a center portion therein.

17. The universal respiratory detector of claim 15, wherein the universal respiratory detector has a longest dimension of less than 1 inch.

18. A universal respiratory detector for detecting a respiratory gas and displaying a respiratory status based on the gas, the respiratory detector comprising:
   a first side and a second side opposite the first side;
   a cover layer, wherein the cover layer covers at least part of a backing; and
   a respiratory sensor layer comprising the backing and a visual indicator on the backing, the visual indicator configured to reversibly change color when a respiratory gas parameter changes and to display the color change, wherein the color change is visible from both the first side and the second side,
   wherein the universal respiratory detector is a sticker, and further wherein the detector is configured to conform to a curved or variable surface contour of an oxygen delivery device or a face of a user and is configured to flex and move together with movement of the oxygen delivery device or the face of the user,
   wherein the universal respiratory detector has a longest dimension of less than 2 inches.

19. The universal respiratory detector of claim 18, wherein the universal respiratory detector has a longest dimension of less than 1 inch.

20. The universal respiratory detector of claim 18, wherein the respiratory indicator is configured to reversibly change color in response to carbon dioxide and to display the color changes for a period of time lasting at least ten hours, further wherein the detector comprises a low or no off-gassing adhesive ring on the second side adhering the respiratory sensor layer to the cover layer, and wherein the adhesive ring has a transparent or translucent region in a center portion therein.

* * * * *